United States Patent
Paul et al.

(10) Patent No.: US 12,248,044 B2
(45) Date of Patent: Mar. 11, 2025

(54) ESTABLISHING PERMITTED GRADIENT INTENSITIES TO PREVENT OVERLOADING OF A MAGNETIC RESONANCE (MR) SYSTEM GRADIENT UNIT

(71) Applicant: Siemens Healthcare GmbH, Erlangen (DE)

(72) Inventors: Dominik Paul, Bubenreuth (DE); Mario Zeller, Erlangen (DE); Flavio Carinci, Würzburg (DE)

(73) Assignee: Siemens Healthineers AG, Erlangen (DE)

( * ) Notice: Subject to any disclaimer, the term of this patent is extended or adjusted under 35 U.S.C. 154(b) by 148 days.

(21) Appl. No.: 18/134,211

(22) Filed: Apr. 13, 2023

(65) Prior Publication Data
US 2023/0349991 A1  Nov. 2, 2023

(30) Foreign Application Priority Data
Apr. 29, 2022  (DE) ............... 10 2022 204 251.4

(51) Int. Cl.
*G01R 33/385* (2006.01)
*A61B 5/055* (2006.01)
*G01R 33/48* (2006.01)

(52) U.S. Cl.
CPC .......... *G01R 33/3852* (2013.01); *A61B 5/055* (2013.01); *G01R 33/4818* (2013.01)

(58) Field of Classification Search
CPC ............ G01R 33/3852; G01R 33/4818; G01R 33/543; G01R 33/385; A61B 5/055
See application file for complete search history.

(56) References Cited

U.S. PATENT DOCUMENTS

| | | | |
|---|---|---|---|
| 2016/0091585 A1* | 3/2016 | Benner | G01R 33/543 324/318 |
| 2016/0091589 A1* | 3/2016 | Benner | G01R 33/543 324/322 |
| 2017/0045594 A1* | 2/2017 | Grodzki | G01R 33/4833 |
| 2017/0205483 A1 | 7/2017 | Feiweier et al. | |
| 2017/0322278 A1* | 11/2017 | Ludwig | G01R 33/543 |

FOREIGN PATENT DOCUMENTS

DE  102016200549 A1  7/2017

* cited by examiner

*Primary Examiner* — Jermele M Hollington
*Assistant Examiner* — Zannatul Ferdous
(74) *Attorney, Agent, or Firm* — Banner & Witcoff Ltd.

(57) ABSTRACT

Permitted gradient intensities are established to prevent an overloading of a gradient unit of a magnetic resonance system during a recording, with the magnetic resonance system, of scan data from an examination object situated in a scan volume of said magnetic resonance system.

17 Claims, 2 Drawing Sheets

15: Gradient establishing unit

User interface

ESTABLISHING PERMITTED GRADIENT INTENSITIES TO PREVENT OVERLOADING OF A MAGNETIC RESONANCE (MR) SYSTEM GRADIENT UNIT

CROSS-REFERENCE TO RELATED APPLICATIONS

The present application claims priority to and the benefit of Germany patent application no. DE 10 2022 204 251.4, filed on Apr. 29, 2022, the contents of which are incorporated herein by reference in their entirety.

TECHNICAL FIELD

The disclosure relates to a method for establishing permitted gradient intensities to prevent an overloading of a gradient unit of a magnetic resonance system during a recording, with said magnetic resonance system, of scan data from an examination object situated in a scan volume of said magnetic resonance system.

BACKGROUND

Magnetic resonance (MR) technology is a known technology with which images of the interior of an examination object can be generated. Expressed simply, for this purpose, the examination object is positioned in a magnetic resonance device in a relatively strong, static, homogeneous main magnetic field, also known as the B0 field, with field strengths of 0.2 tesla to 7 tesla or more, so that its nuclear spins become oriented along the main magnetic field. In order to trigger nuclear spin resonances that are measurable as signals, high frequency excitation pulses (RF pulses) are radiated into the examination object and the nuclear spin resonances produced are measured as so-called k-space data and, on the basis thereof, MR images are reconstructed or spectroscopic data is determined.

For position encoding of the scan data, rapidly switched magnetic gradient fields, known as gradients for short, are overlaid on the main magnetic field. A scheme that is used which describes a temporal sequence of RF pulses to be radiated in and gradients to be switched is known as a pulse sequence (scheme), or sequence for short. The recorded scan data is digitized and stored as complex number values in a k-space matrix. From the k-space matrix populated with values, an associated MR image can be reconstructed, for example, by means of a multi-dimensional Fourier transform.

A gradient unit of a magnetic resonance system that is used for generating the gradient fields typically comprises three physical gradient axes, which can be designated the x-, y- and z-axes. In a magnetic resonance system with a cylindrical region for receiving a support on which an examination object to be examined is arranged for an MR scan, the z-axis often corresponds to the cylinder axis of the receiving region. A vertical axis, which is perpendicular to the z-axis, is often defined as the y-axis, and a horizontal axis perpendicular to the y-axis and the z-axis as the x-axis.

Typically, on each of the three physical gradient axes, only a limited gradient intensity, specifically a maximum specified gradient intensity GS can be applied, and this is typically specified in the units mT/m. The value of a maximum specified gradient intensity is often the same in all three physical gradient axes.

SUMMARY

Logical gradient axes can be distinguished from the physical gradient axes. The logical gradient axes typically comprise a slice-selection gradient axis, a phase-encoding gradient axis, and a frequency-encoding gradient axis, which typically form a three-dimensional orthogonal coordinate system. The orientation of a field of view (FOV) typically specifies the relative position of the logical gradient axes in relation to the physical gradient axes, which can usually be represented as a rotation.

Typically, dependent upon the orientation of the field of view, the logical gradient axes therefore deviate by a rotation from the physical gradient axes so that the gradients of the logical gradient axes that are to be switched are distributed dependent upon the orientation of the field of view on the physical gradient axes.

In order, for clinical uses, in all cases of rotations of the logical gradient axes relative to the physical gradient axes that are predetermined by every possible orientation of the field of view, and of superpositions of gradient activities from the logical gradient axes onto the physical gradient axes, to avoid an interruption of examination protocols by overloading the gradient unit, as a convention, a permitted usable gradient intensity $G_N$ is restricted, dependent upon the already defined maximum specified gradient intensity $G_S$, to:

$$G_N < G_S/\mathrm{SQRT}(3) \qquad (KV),$$

where SQRT(3) is the square root of the number 3, which results geometrically from the three spatial directions (Pythagoras' theorem in 3D). By way of a restriction to such a permitted usable gradient intensity $G_N$, for each possible rotation of the physical gradient axes relative to the logical gradient axes, it is ensured that a gradient intensity needed in a physical gradient axis does not exceed the maximum specified gradient intensity $G_S$.

For example, at a maximum specified gradient intensity of $G_S=40$ mT/m, for the logical gradient axes, there results for the usable gradient intensity $G_N=23$ mT/m. The actual usable gradient intensity $G_N$ is therefore significantly lower than the maximum specified gradient intensity $G_S$, and therefore all the desired examination protocols should be executable with all possible orientations of the field of view. In order to prevent interruptions to examination protocols in a reliable way, the maximum usable gradient intensity $G_N$ determined via the convention KV is also often rounded down.

In order to shorten a time needed for a scan, it is known to establish a permitted gradient intensity on the frequency-encoding gradient axis, which is relevant for the readout duration, to be somewhat larger than is actually permitted by the convention. Therein, it can however occur that examination protocols do become interrupted or do not even start, since the gradient unit is indeed overloaded in at least one physical gradient axis by a demand for a non-achievable gradient intensity that has thus become possible. As a countermove to such an exceeding of the convention on the frequency-encoding gradient axis, the permitted gradient intensity for the slice-selection gradient axis and the phase-encoding gradient axis is often selected to be somewhat lower than is permitted by the convention, to make overloading of the gradient unit less likely.

Thus, for example, at a maximum specified gradient intensity of $G_S=40$ mT/m for the frequency-encoding gradient axis, a permitted gradient intensity $G_{Nr}=24$ mT/m, and for both the slice-selection gradient axis and the phase-encoding gradient axis $G_{Ne}=22$ mT/m, can be established.

However, it is not precluded that a stated overloading can occur for particular orientations of the field of view. In addition, the permitted gradient intensities are still far removed from the maximum specified gradient intensity, so that all examination protocols are carried out with significantly weaker usable gradient intensities according to the convention KV and thus only significantly slower than with the associated maximum specified gradient intensity.

DE102016200549 A1 discloses a method in which, dependent upon the orientation of the field of view, an optimized, maximum permitted gradient intensity is calculated by testing and adapting the examination protocol. The method proposed in DE102016200549 A1 is, however, computation-intensive and therefore time-intensive. This means that even before the actual start of an examination protocol, an additional time demand arises through the testing and adapting, which once again can reduce or even use up the time gain from the optimized gradient intensities.

It is therefore an object of the present disclosure to provide a method for recording magnetic resonance data, a magnetic resonance system, a computer program, and an electronically readable data carrier which permit an optimized utilization of maximum specified gradient intensities without the stated disadvantages.

The object is achieved by way of the embodiments as discussed herein, including the claims.

A method according to the disclosure for establishing permitted gradient intensities to prevent an overloading of a gradient unit of a magnetic resonance system during a recording, with the magnetic resonance system, of scan data from an examination object situated in a scan volume of said magnetic resonance system comprises the steps:

loading an examination protocol with which scan data is to be recorded, loading a list of at least three rotation classes, wherein associated with each rotation class is a rotation range between a minimum rotation angle and a maximum rotation angle, wherein the rotation ranges of the rotation classes do not overlap and all the rotation classes altogether cover the entire region lying between the minimum rotation angle and the maximum rotation angle, and wherein a gradient intensity is associated with each rotation class, establishing a field of view of the examination object from which scan data is to be recorded, wherein the orientation of the field of view is also established, determining a rotation which describes a relative position of logical gradient axes established by way of the orientation of the field of view to the physical gradient axes of the gradient unit, establishing maximum permitted gradient intensities for the loaded examination protocol dependent upon the rotation as determined using the loaded list of rotation classes, recording scan data from the field of view using the examination protocol with the established maximum permitted gradient intensities.

The proposed accessing of a list of rotation classes with associated gradient intensities permits an improved utilization of the gradient intensities available to the gradient unit on the physical gradient axes with little computational effort, since a complex testing of possible gradient intensities can be dispensed with. With a higher permitted gradient intensity, a scan duration of a recording of scan data can be reduced with the permitted gradient intensity. Since fields of view (FOV) do not lead in every case to a rotation of the logical gradient axes relative to the physical gradient axes, it is not necessary in every case to rotate examination protocols severely relative to the physical gradient axes in accordance with the logical gradient axes, nor through a plurality of axes. An available power level is divided into the different rotation classes, which themselves are intrinsically stable.

A magnetic resonance system according to the disclosure comprises a magnet unit, a gradient unit, a high frequency unit, and a control facility configured to perform a method according to the disclosure with a gradient establishing unit.

A computer program according to the disclosure implements a method according to the disclosure on a control facility, when the computer program is executed on the control facility.

The computer program described herein may also be present in the form of a computer program product, which can be directly loaded into a memory store of a control facility, having program code means in order to carry out any methods according to the disclosure when the computer program product is executed in the computing unit of the computing system.

An electronically readable data carrier (e.g. non-transitory computer-readable medium) according to the disclosure may comprise the physical medium and/or electronically readable control information stored thereon, which comprises at least one computer program according to the disclosure and is configured such that, when the data carrier is used in a control facility of a magnetic resonance system, it carries out any methods according to the disclosure.

The advantages and embodiments set out in relation to the method apply accordingly for the magnetic resonance system, the computer program product, and the electronically readable data carrier.

BRIEF DESCRIPTION OF THE DRAWINGS

Further advantages and details of the present disclosure are disclosed in the following description of exemplary embodiments and by reference to the drawings. The examples given do not represent restrictions of the disclosure. In the drawings.

DETAILED DESCRIPTION OF THE DISCLOSURE

Figure 1:
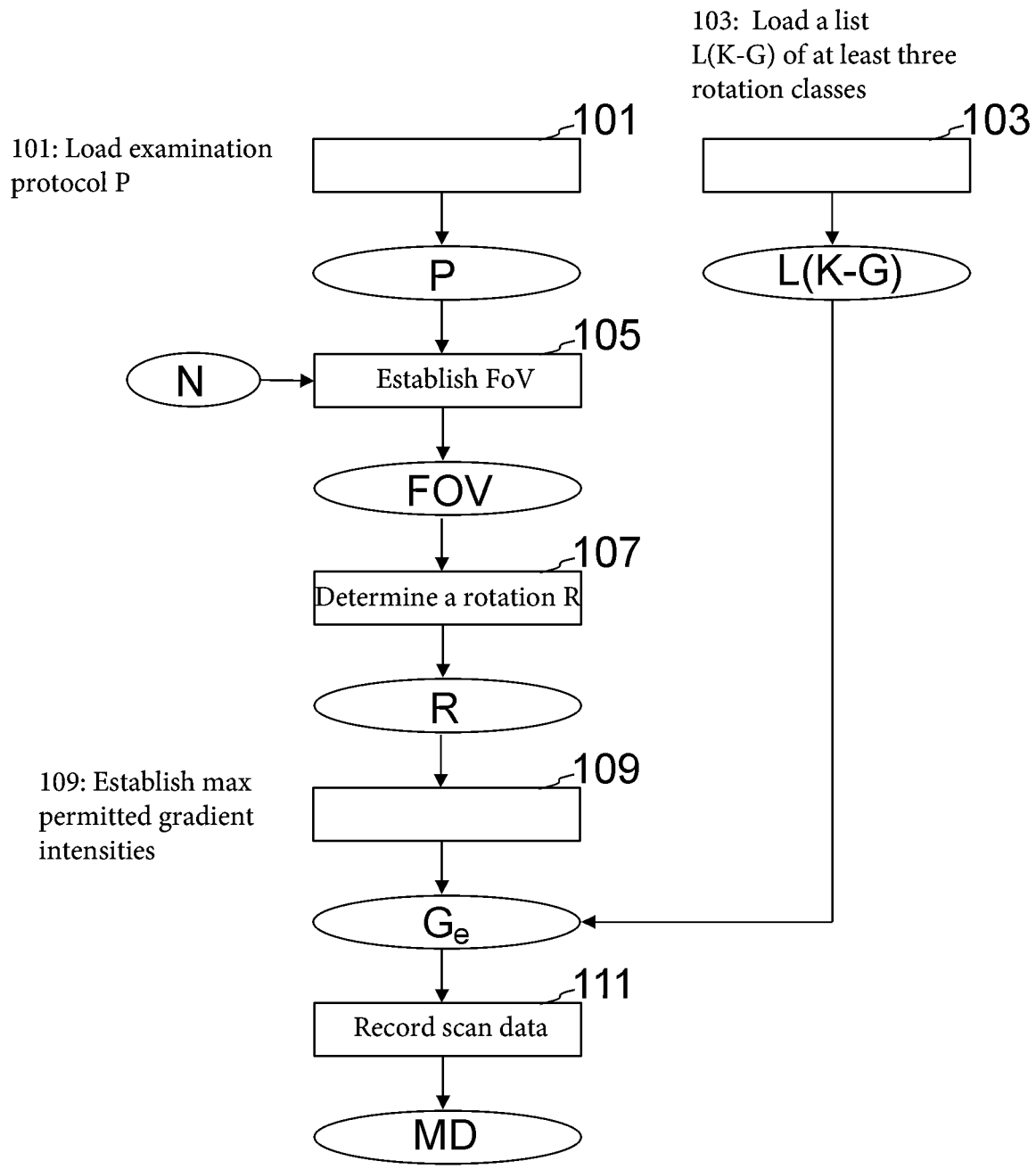
FIG. 1 illustrates an example flow diagram of a method according to one or more embodiments of the disclosure.

FIG. 1 shows a schematic flow diagram of a method according to the disclosure for establishing permitted gradient intensities $G_e$ on physical gradient axes of a gradient unit of a magnetic resonance system 1 during a recording, with the magnetic resonance system 1, of scan data MD from an examination object U situated in a scan volume of said magnetic resonance system 1.

An examination protocol P, with which scan data is to be recorded, is loaded (block 101). The examination protocol comprises an examination target which establishes which data is to be recorded from where, and can specify at least one pulse sequence to be used during the recording of the scan data MD.

A list L(K-G) of at least three rotation classes is loaded (block 103), wherein associated with each rotation class K is a rotation range RB(K) lying between a minimum rotation angle R1 and a maximum rotation angle R2, wherein the rotation ranges RB(K) of the rotation classes K do not overlap, and all the rotation classes K with their rotation ranges RB(K) altogether cover the entire region lying between the minimum rotation angle R1 and the maximum rotation angle. Associated herein with each rotation class K is a permitted gradient intensity G for this rotation class K.

The minimum rotation angle R1 can be a rotation angle of 0°. This corresponds to a (strict) axial orientation along a physical gradient axis. The maximum rotation angle R2 can be a rotation angle of 45°. This corresponds to a maximum deviation from a physical gradient axis. With a selection of this type, an overall possible region of rotation angles is covered by the rotation classes.

Herein, in a simple case, the rotation ranges RB(K) of the rotation classes K can each cover equal-sized angular ranges of the region between the minimum rotation angle R1 and the maximum rotation angle R2. Thus, an equidistant coverage of the full region between the minimum rotation angle R1 and the maximum rotation angle R2 can be achieved.

Another distribution of the region between the minimum rotation angle R1 and the maximum rotation angle R2 into the rotation classes K is conceivable, for example, also with any desired steps in the coverage of the region between the minimum rotation angle R1 and the maximum rotation angle R2 through the rotation ranges RB(K) of the rotation classes K.

For example, the rotation class K, the rotation range RB(K) of which comprises the minimum rotation angle R1 can include exactly the minimum rotation angle R1 as the rotation range RB(K). Thus, a gradient intensity G associated with the rotation class K, the rotation range RB(K) of which includes the minimum rotation angle R1 would be permitted precisely for fields of view with a strictly axial orientation along the physical gradient axis.

The rotation class K, the rotation range RB(K) of which includes the minimum rotation angle R1 can, however, also be selected somewhat more generously and includes, for example, as the rotation range RB(K), a region from the minimum rotation angle R1 to an angle of a half, one, or three, not more than five degrees removed from the first rotation angle, etc. Similarly, the rotation range RB(K) of the rotation class K, the rotation range RB(K) of which includes the minimum rotation angle R1 which covers, starting from the minimum rotation angle R1, approximately one, two or nine, not more than eleven percent of the region between the minimum rotation angle R1 and the maximum rotation angle R2 could be selected as the rotation range RB(K), etc.

Similarly, the rotation class K, the rotation range RB(K) of which comprises the maximum rotation angle R2, can include exactly the maximum rotation angle R2 as the rotation range RB(K). Thus, a gradient intensity G associated with the rotation class K, the rotation range RB(K) of which includes the maximum rotation angle R2, would be permitted precisely for fields of view with an orientation maximally rotated away from the physical gradient axis.

The rotation class K, the rotation range RB(K) of which includes the maximum rotation angle R2 can, however, also be selected somewhat more generously and includes, for example, as the rotation range RB(K), a region from the maximum rotation angle R2 to an angle of a half, one, three or a maximum of five degrees removed from the first rotation angle, etc. Similarly the rotation angle RB(K) of the rotation class K, the rotation range RB(K) of which includes the maximum rotation angle R2 which covers, starting from the minimum rotation angle R1, approximately one, two or nine, not more than eleven percent of the region between the minimum rotation angle R1 and the maximum rotation angle R2 can be selected as the rotation range RB(K), etc.

As the gradient intensity G, a maximum specified gradient intensity of the gradient unit can be associated with the rotation class K, the rotation range RB(K) of which includes the minimum rotation angle R1. It is thus established that for this rotation class K, the rotation range RB(K) of which includes the minimum rotation angle R1, the full maximum specified gradient intensity can be used.

As the gradient intensity G, a maximum specified gradient intensity of the gradient unit divided by the value of the square root of the number three can be associated with the rotation class K, the rotation range of which includes the maximum rotation angle. It is thus established that for this rotation class K, the rotation range RB(K) of which includes the minimum rotation angle R2, only a usable maximum gradient intensity determined by the convention KV can be used.

For a rotation class K, the rotation range RB(K) of which includes neither the minimum rotation angle R1 nor the maximum rotation angle R2, as the permitted gradient intensity G, a gradient intensity can be assigned which lies between the maximum specified gradient intensity of the gradient unit and the maximum specified gradient intensity of the gradient unit divided by the value of the square root of the number three. For example, a gradient intensity associated with a rotation class K, the rotation range RB(K) of which includes neither the minimum rotation angle R1 nor the maximum rotation angle R2, can be determined according to a spacing of the rotation range RB(K) from the minimum rotation angle R1 and/or from the maximum rotation angle R2, from the maximum specified gradient intensity and/or from the scaled gradient intensity determined from the usable maximum gradient intensity by the convention KV.

Associated with each of the rotation classes K are gradient intensities G that are determined such that they lead to an overloading on a physical gradient axis for no rotation R that is included in the rotation range RB(K). A determination of such gradient intensities G associated with the rotation classes K can take place, similarly to the convention KV, on the basis of geometric considerations. Alternatively, the gradients G associated with the rotation classes K can be somewhat less strictly determined in that, at the most, for a low percentage of not more than 1% of the rotations included in the rotation range of the rotation class, for example, an overloading can occur on a physical gradient axis. Thus the probability of an overloading is at least very low and a still better utilization of the gradient intensities can take place.

The list L(K-G) loaded can comprise, for example, at least six rotation classes K. The more rotation classes K that are included in the list L(K-G), the higher is the flexibility achievable through the use of the list L(K-G) in the optimization of the utilization of the gradient intensity. However, as the number of rotation classes increases, the complexity of the determination of the maximum permitted gradient intensities Ge and the adaptation to be performed of the parameters of the pulse sequence used according to the determined maximum permitted gradient intensity $G_e$ also increases.

A field of view FOV of the examination object U, from which scan data MD is to be recorded, is established (block 105). Therein, the orientation of the field of view FOV relative to the physical gradient axes is simultaneously established.

The establishing of the field of view FOV can be undertaken by a user N who, for example, positions a desired field of view in a previously recorded scout view of the examination object and for example orients it along structures in the examination object that are desired to be represented, and so establishes it as the field of view FOV to be used. A user can herein be notified that a user-established orientation of the field of view FOV relative to the physical gradient axes influences a scan duration required for the recording of the scan data MD. It can be offered to the user optionally, for example, to leave the orientation of the field of view FOV fixed along the physical gradient axes in order to achieve a shorter scan duration.

It is also conceivable that the field of view FOV of the examination object U is established dependent upon the loaded examination protocol P. For instance, an orientation of the field of view FOV can already be established by way of the loaded examination protocol P, but also a position of a field of view FOV can be specified, for example, as central in a scan volume of the magnetic resonance system 1.

For example, for examination protocols P for which, for the underlying clinical objective, no specific orientation of the field of view FOV is required, a strictly axial orientation of the field of view FOV to the physical gradient axes can be established by way of the examination protocol P. This is, for example, often the case for recordings of scan data in an abdominal region of a patient as the examination object U, since then in any event a great deal of anatomy is examined with different orientations. In this way, it is ensured that a required scan duration is kept as short as possible without impairing the quality of the recorded scan data MD. For example, recordings of scan data in an abdominal region of a patient as the examination object U are often time-critical and benefit from shortened scan durations, especially if a patient must hold his breath for the recording.

A rotation that describes a relative position of logical gradient axes established by way of the orientation of the field of view to the physical gradient axes of the gradient unit is determined (block 107). Techniques and mathematical operations used for this purpose are known.

Maximum permitted gradient intensities Ge for the loaded protocol are established dependent upon the rotation as determined and using the loaded list of rotation classes (block 109).

To achieve this, it can be determined in which of the rotation classes K of the list L(K-G) the determined rotation R lies, and the gradient intensity G associated with this rotation class K as the maximum permitted gradient intensity $G_e$ is automatically established.

Using the examination protocol P, and with the established maximum permitted gradient intensities $G_e$, scan data MD is recorded from the field of view FOV of the examination object U (block 111). The recorded scan data MD can be stored or further processed. For example, image data can be reconstructed from the recorded scan data MD, and optionally displayed via a suitable device (e.g. the user interface as discussed with respect to FIG. 2).

The method described can also be applied separately for all physical gradient axes.

By way of the use of rotation classes K with associated gradient intensities which prevents an overloading of the gradient unit and simultaneously permits a better utilization of the gradient intensities available by way of the gradient unit, a scan duration of recordings of scan data can be shortened.

For example, for a magnetic resonance device with a maximum specified gradient intensity of $G_S$=33 mT/m for which previously only examination protocols of a maximum usable gradient intensity of $G_N$=17 mT/m were carried out, for example, when using a VIBE pulse sequence, the parameters echo time TE and repetition time TR of TE/TR=1.84 ms/4.4 ms at a gradient intensity of 17 mT/m on establishment of an orientation of the field of view and association with the corresponding rotation class with a gradient intensity of 30 mT/m for example can be reduced to TE/TR=1.36 ms/3.5 ms. It can therefore be achieved, for example, that a patient has to hold his breath a few seconds less for the recording of the scan data. A savings of, for example, just two seconds during breath holding can make the difference, in particular in sick patients, between a successful recording and a respiration-blurred recording that has to be repeated.

Figure 2:
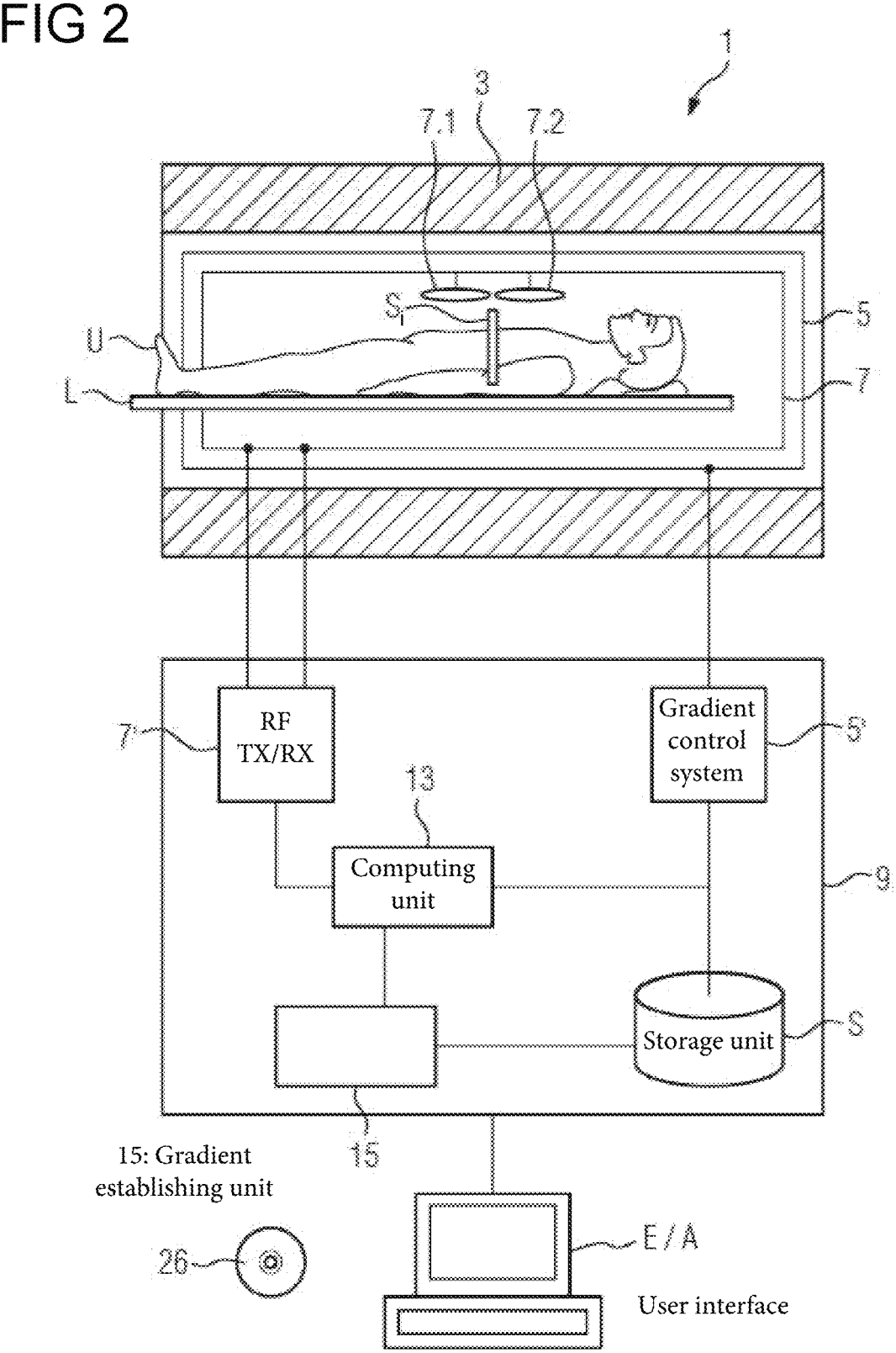
FIG. 2 illustrates an example magnetic resonance system according to one or more embodiments of the disclosure.

FIG. 2 shows schematically a magnetic resonance system 1 according to the disclosure. This comprises a magnet unit 3 for generating the main magnetic field, a gradient unit 5 (e.g. gradient coils) for generating the gradient fields, a high frequency (also known as a radio-frequency of RF) unit 7 for radiating in and receiving high frequency (also known as RF) signals and a control facility 9 configured for carrying out a method according to the disclosure.

In FIG. 2, these subunits of the magnetic resonance system 1 are shown only roughly schematically. In particular, the RF unit 7 can consist of a plurality of subunits, for example, a plurality of coils such as the schematically shown coils 7.1 and 7.2 or more coils which can be configured either only to transmit RF signals or only to receive the triggered RF signals, or for both.

In order to examine an examination object U, for example, a patient or a phantom, the examination object can be introduced on a support L into the magnetic resonance system 1, in the scanning volume thereof. The slice or the slab $S_i$ represents an exemplary target volume of the examination object from which echo signals are to be recorded and captured as scan data.

The control facility 9 (also referred to herein as a control computer, a controller, or controller circuitry) serves to control the magnetic resonance system 1 and can, for example, control the gradient unit 5 by means of a gradient control system 5' and the RF unit 7 by means of a RF transmitting/receiving control system 7'. The RF unit 7 can herein comprise a plurality of channels on which signals can be transmitted or received.

The RF unit 7 is responsible, together with its RF transmitting/receiving control system 7' for the generation and radiating-in (transmission) of a RF alternating field for manipulation of the spins in a region to be manipulated (for example, in slices S to be scanned) of the examination object U. Herein, the center frequency of the RF alternating field, also designated the B1 field, is typically adjusted so that, as far as possible, it lies close to the resonance frequency of the spin to be manipulated. Deviations of the center frequency from the resonance frequency are referred to as off-resonance. In order to generate the B1 field, in the RF unit 7, currents controlled by means of the RF transmitting/receiving control system 7' are applied to the RF coils.

Furthermore, the control facility 9 comprises a gradient establishing unit 15, with which maximum permitted gradient intensities are established according to the disclosure dependent upon a rotation determined from an orientation of a field of view and making use of a list of rotation classes described herein. For instance, the gradient establishing unit 15 has access to at least one list of rotation classes. The control facility 9 is configured overall to carry out a method according to the disclosure.

A computing unit 13 included in the control facility 9 is configured to carry out all the computation operations necessary for the required scans and determinations. Intermediate results and results needed for this or determined herein can be stored in a storage unit S of the control facility 9. The units mentioned are herein not necessarily to be understood as physically separate units, but represent merely a subdivision into units of purpose which, however, can also be realized, for example, in fewer, or even only in one single, physical unit.

By way of an input/output facility E/A (also referred to herein as a user interface or an input/output interface) of the magnetic resonance system 1, for example, control commands can be passed by a user to the magnetic resonance system and/or results from the control facility 9 such as, for example, image data can be displayed.

A method described herein can also exist in the form of a computer program product which comprises a program and implements any of the methods described herein on a control facility 9 when said program is executed on the control facility 9. An electronically readable data carrier 26 (e.g. a non-transitory computer-readable medium) with electronically readable control information stored thereon can also be provided, said control information comprising at least one computer program product as described above and being configured to carry out any of the methods described herein when the data carrier 26 is used in a control facility 9 of a magnetic resonance system 1.

The various components described herein may be referred to as "units." Such components may be implemented via any suitable combination of hardware and/or software components as applicable and/or known to achieve their intended respective functionality. This may include mechanical and/or electrical components, processors, processing circuitry, or other suitable hardware components, in addition to or instead of those discussed herein. Such components may be configured to operate independently, or configured to execute instructions or computer programs that are stored on a suitable computer-readable medium. Regardless of the particular implementation, such units, as applicable and relevant, may alternatively be referred to herein as "circuitry," "controllers," "processors," or "processing circuitry," or alternatively as noted herein.

What is claimed is:

1. A method performed by a magnetic resonance (MR) system, comprising:
    loading an examination protocol with which scan data is to be recorded;
    loading a list of at least three rotation classes, each rotation class from among the at least three rotation classes being associated with (i) a rotation range between a first rotation angle and a second rotation angle, and (ii) a gradient intensity;
    wherein the rotation ranges of each one of the at least three rotation classes do not overlap with one another and together cover a region between the first rotation angle and the second rotation angle;
    establishing a field of view (FoV) of an examination object situated in a scan volume of the MR system from which the scan data is to be recorded;
    establishing an orientation of the FoV;
    determining a rotation that describes a relative position of logical gradient axes, established by way of the orientation of the FoV to physical gradient axes of a gradient unit of the MR system;
    establishing permitted gradient intensities for the loaded examination protocol dependent upon the determined rotation using the loaded list of the at least three rotation classes;
    recording the scan data from the FoV using the examination protocol with the established permitted gradient intensities;
    reconstructing, from the recorded scan data, image data; and
    displaying the image data.

2. The method as claimed in claim 1, wherein the permitted gradient intensities for the loaded examination protocol comprise maximum permitted gradient intensities.

3. The method as claimed in claim 1, wherein the first rotation angle is a rotation angle of 0° and the second rotation angle is a rotation angle of 45°.

4. The method as claimed in claim 1, wherein the rotation range of each respective one of the at least three rotation classes cover an equal-sized angular range of the region between the first rotation angle and the second rotation angle.

5. The method as claimed in claim 1, wherein one of the at least three rotation classes is associated with a gradient intensity comprising a maximum predetermined gradient intensity of the gradient unit and has a respective rotation range that comprises the first rotation angle.

6. The method as claimed in claim 1, wherein one of the at least three rotation classes is associated with a gradient intensity comprising a maximum predetermined gradient intensity of the gradient unit divided by a value of a square root of three, and has a respective rotation range that comprises the first rotation angle.

7. The method as claimed in claim 1, wherein one of the at least three rotation classes is associated with a gradient intensity between a maximum predetermined gradient intensity of the gradient unit and the maximum predetermined gradient intensity of the gradient unit divided by a value of a square root of three, and has a respective rotation range that comprises neither the first rotation angle nor the second rotation angle.

8. The method as claimed in claim 1, wherein one of the at least three rotation classes is associated with a gradient intensity that is determined to cause an overloading on a physical gradient axis for a rotation angle that is not included in the respective rotation range.

9. The method as claimed in claim 1, wherein one of the at least three rotation classes is associated with a gradient intensity that is determined to cause an overloading on a physical gradient axis for rotation angles of not more than 1% of the rotations included in the respective rotation range.

10. The method as claimed in claim 1, wherein one of the at least three rotation classes having a respective rotation range that comprises the first rotation angle comprises only the first rotation angle.

11. The method as claimed in claim 1, wherein one of the at least three rotation classes having a respective rotation range that comprises the first rotation angle comprises a region of five degrees from the first rotation angle.

12. The method as claimed in claim 1, wherein one of the at least three rotation classes having a respective rotation range that comprises the second rotation angle comprises only the second rotation angle.

13. The method as claimed in claim 1, wherein one of the at least three rotation classes having a respective rotation range that comprises the second rotation angle comprises a region of five degrees from the second rotation angle.

14. The method as claimed in claim 1, wherein the FoV of the examination object and the orientation of the established FoV are each established dependent upon the loaded examination protocol.

15. The method as claimed in claim 1, wherein the loaded list comprises at least six rotation classes.

16. A magnetic resonance (MR) system, comprising:
a gradient unit; and
control circuitry configured to:
- load an examination protocol with which scan data is to be recorded;
- load a list of at least three rotation classes, each rotation class from among the at least three rotation classes being associated with (i) a rotation range between a first rotation angle and a second rotation angle, and (ii) a gradient intensity;
- wherein the rotation ranges of each one of the at least three rotation classes do not overlap with one another and together cover a region between the first rotation angle and the second rotation angle;
- establish a field of view (FoV) of an examination object situated in a scan volume of the MR system from which the scan data is to be recorded;
- establish an orientation of the FoV;
- determine a rotation that describes a relative position of logical gradient axes, established by way of the orientation of the FoV to physical gradient axes of a gradient unit of the MR system;
- establish permitted gradient intensities for the loaded examination protocol dependent upon the determined rotation using the loaded list of the at least three rotation classes;
- record the scan data from the FoV using the examination protocol with the established permitted gradient intensities;
- reconstruct, from the recorded scan data, image data; and
- display the image data.

17. A non-transitory computer-readable medium having instructions stored thereon that, when executed by control circuitry of a magnetic resonance (MR) system, cause the MR system to:
- load an examination protocol with which scan data is to be recorded;
- load a list of at least three rotation classes, each rotation class from among the at least three rotation classes being associated with (i) a rotation range between a first rotation angle and a second rotation angle, and (ii) a gradient intensity,
- wherein the rotation ranges of each one of the at least three rotation classes do not overlap with one another and together cover a region between the first rotation angle and the second rotation angle;
- establish a field of view (FoV) of an examination object situated in a scan volume of the MR system from which the scan data is to be recorded;
- establish an orientation of the FoV;
- determine a rotation that describes a relative position of logical gradient axes, established by way of the orientation of the FoV to physical gradient axes of a gradient unit of the MR system;
- establish permitted gradient intensities for the loaded examination protocol dependent upon the determined rotation using the loaded list of the at least three rotation classes;
- record the scan data from the FoV using the examination protocol with the established permitted gradient intensities;
- reconstruct, from the recorded scan data, image data; and
- display the image data.

* * * * *